US00PP24777P3

(12) United States Plant Patent
Zaiger et al.

(10) Patent No.: US PP24,777 P3
(45) Date of Patent: Aug. 19, 2014

(54) PEACH TREE NAMED 'SUMMER AMELIA'

(50) Latin Name: *Prunus persica*
Varietal Denomination: Summer Amelia

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 240 days.

(21) Appl. No.: 13/506,165

(22) Filed: Apr. 2, 2012

(65) Prior Publication Data

US 2013/0263342 P1 Oct. 3, 2013

(51) Int. Cl.
*A01H 5/00* (2006.01)

(52) U.S. Cl.
USPC ..... Plt./197

(58) Field of Classification Search
USPC ..... Plt./197
See application file for complete search history.

(56) References Cited

PUBLICATIONS

Hen House Market, vol. 3, issue 7, Aug. 9, 2008, retrieved from the internet on Dec. 3, 2013 at <http://www.ckt.net/goodnatured/our_story/newsletters/2008_08_09%20Bader%20Farms.pdf>, 2 pp.*
"Grafting and Propagating Fruit Trees" prepared by R.M. Crasweller, Pennsylvania State University, 2005, retrieved from the Internet on Dec. 5, 2013 at <http://pubs.cas.psu.edu/FreePubs/pdfs/UJ255.pdf>, 21 pp.*
Dozier, W.A. et. al., "Peach and Nectarine Varietal Performance in the Wiregrass Area of Alabama", Bulletin 570, 1985, retrieved from the internet on Dec. 5, 2013 at <http://aurora.auburn.edu/repo/bitstream/handle/11200/2489/1749BULL.pdf?sequence=1>, 28 pp.*

* cited by examiner

*Primary Examiner* — June Hwu
*Assistant Examiner* — Louanne Krawczewicz Myers

(57) ABSTRACT

A new and distinct variety of peach tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Regular and productive bearer of large size fruit.
3. Fruit with a high degree of attractive red skin color.
4. Firm, yellow flesh with good flavor and eating quality.
5. Fruit being relatively uniform in size throughout the tree.

1 Drawing Sheet

Botanical designation: *Prunus persica.*
Variety denomination: 'Summer Amelia'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach trees, which are known to us, and mentioned herein, 'Sweet Henry' Peach (U.S. Plant Pat. No. 16,068) 'Tra-Zee' Peach (U.S. Plant Pat. No. 6,347).

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. from open pollinated seed collected from 'Sweet Henry' Peach (U.S. Plant Pat. No. 16,068). We planted and maintained a large group of these open pollinated seedlings on their own root system and under close and careful evaluation we recognized the desirable tree and fruit characteristics of the present new variety and selected it in 2008 for further asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of peach tree is of large size, vigorous, upright growth and a regular and productive bearer of large size, firm, yellow flesh, clingstone fruit. The fruit is further characterized by having good flavor and eating quality, having a high degree of attractive red skin color and being relatively uniform in size throughout the tree. In comparison to its seed parent 'Sweet Henry' Peach (U.S. Plant Pat. No. 16,068) the fruit of the new peach variety has traditional acid flavor compared to subacid and is approximately 2 days later in maturity. In comparison to the commercial variety 'Tra-Zee' Peach (U.S. Plant Pat. No. 6,347) the fruit of the new variety has a higher degree of attractive red skin color and is approximately 12 days earlier in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 4 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 4 year old specimens grown near Modesto, Calif., with color in accordance with Munsell Book of Color.

Tree:

*Size*.—Large, usually pruned to 3 to 3.5 meters in height and width for economical harvesting of fruit. Varies with different cultural practices.

*Vigor*.—Vigorous, growth of 1.5 to 2 meters in height the first growing season. Varies slightly with soil type, fertility and cultural practices.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 3 consecutive years. No alternate bearing observed.

*Fertility*.—Self-fertile.

*Density*.—Medium dense, usually pruned to vase shape to increase air movement and sunlight to the center of the tree to enhance fruit color and health of fruit spurs.

*Hardiness*.—Hardy in all stone fruit growing areas of California. Tree grown in USDA Hardiness Zone 9. Winter chilling requirement approximately 800 hours at or below 45° F.

Trunk:

*Size*.—Medium. Average circumference 40.3 cm at 22.9 cm above ground on a 5 year old tree.

*Stocky*.—Medium stocky.

*Texture*.—Medium shaggy, roughness increases with age.

*Color*.—Varies from 2.5Y 5/4 to 5Y 6/2.

Branches:

*Size*.—Medium. Average circumference 14.2 cm at 1.2 meters above ground. Crotch angle approximately 35°, increases with crop load.

*Surface texture*.—New growth relatively smooth. Mature growth medium rough, roughness increases with age.

*Lenticels*.—Average number 46 in a 25.8 sq cm section. Average length 3.7 mm. Average width 1.5 mm. Color varies from 10YR 7/6 to 10YR 7/8.

*Color*.—New growth varies from 2.5GY 7/8 to 2.5GY 6/8. Mature growth varies from 7.5YR 4/4 to 10YR 3/6, varies with age of growth.

Leaves:

*Size*.—Medium to large. Average length 133.8 mm. Average width 38.2 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, small ridges created by midrib and pinnate venation. Both surfaces glabrous.

*Petiole*.—Average length 9.9 mm. Average width 1.6 mm. Longitudinally grooved. Surface glabrous. Color varies from 2.5GY 7/8 to 2.5GY 6/8.

*Glands*.—Reniform. Size — small to medium. Average length 1.1 mm. Average diameter 0.8 mm. Average number 3, varies from 1 to 4. Located primarily on lower portion of the leaf blade and the upper portion of the petiole. Color varies from 2.5GY 7/8 to 2.5GY 6/8.

*Stipules*.—None present.

*Color*.—Upper surface varies from 7.5GY 4/4 to 7.5GY 3/4. Lower surface varies from 5GY 4/6 to 5GY 5/6. Midvein color varies from 2.5GY 9/4 to 2.5GY 8/4.

Flower buds:

*Size*.—Medium to large. Average length 17.1 mm. Average diameter 10.9 mm.

*Hardiness*.—Hardy with respect to California winters.

*Form*.—Conical, becoming elongated before opening.

*Pedicel*.—Average length 3.0 mm. Average width 1.5 mm. Color varies from 2.5GY 7/6 to 5GY 6/6.

*Color*.—Varies from 10RP 7/8 to 7.5RP 7/6.

Flowers:

*Blooming period*.—Date of First Bloom Feb. 18, 2011. Date of Petal Fall Feb. 28, 2011, varies slightly with climatic conditions.

*Size*.—Large, showy. Average height 21.6 mm. Average diameter 45.8 mm.

*Petals*.—Normally 5, alternately arranged to sepals. Size — large. Average length 25.2 mm. Average width 20.3 mm. Form — nearly globose, base narrows at point of attachment. Margin — sinuate. Both upper and lower surfaces glabrous. Color varies from 7.5RP 8/4 to 7.5RP 7/6.

*Sepals*.—Normally 5, alternately arranged to petals. Size — large. Average length 7.5 mm. Average width 7.1 mm. Shape — triangular, apex rounded. Margin — entire. Surface — upper surface glabrous, lower surface pubescent. Color — upper surface varies from 5GY 5/6 to 7.5R 4/6. Lower surface varies from 7.5R 3/2 to 7.5R 2/4.

*Stamens*.—Average number per flower 42, varies from 38 to 44. Average filament length 17.1 mm. Filament color varies from N 9.5/ (white) to 7.5RP 5/8. Anther color varies from 5Y 8/6 to 7.5R 3/8.

*Pollen*.—Self-fertile. Color varies from 2.5Y 7/12 to 5Y 7/10.

*Pistil*.—Normally 1. Surface — pubescent. Average length 19.1 mm. Position of the stigma even with anthers. Color varies from 10Y 8/6 to 2.5GY 8/6.

*Fragrance*.—Heavy aroma.

*Color*.—Varies from 7.5RP 8/4 to 7.5RP 7/6.

*Number flowers per flower bud*.—One.

*Pedicel*.—Average length 4.3 mm. Average width 1.6 mm. Color varies from 2.5GY 7/8 to 2.5GY 6/8.

Fruit:

*Maturity when described*.—Firm ripe.

*Date of first picking*.—Aug. 13, 2011.

*Date of last picking*.—Aug. 23, 2011, varies slightly with climatic conditions.

*Size*.—Large. Average diameter axially 63.7 mm. Average transversely in suture plane 75.2 mm. Average weight 224.4 grams, varies slightly with fertility of the soil, amount of thinning and climatic conditions.

*Form*.—Globose.

*Suture*.—Distinct, extends from base to apex.

*Ventral surface*.—Lipped, well sealed.

*Apex*.—Slightly retuse.

*Base*.—Retuse.

*Stem cavity*.—Rounded to slightly elongated in suture plane. Average depth 8.4 mm. Average diameter 10.0 mm.

Stem:

*Size*.—Medium. Average length 10.8 mm. Average diameter 2.9 mm.

*Color*.—Varies from 2.5GY 6/8 to 5GY 6/6.

Flesh:

*Ripens*.—Evenly.

*Texture*.—Firm, meaty, crisp.

*Fibers*.—Few, small, tender.

*Firmness*.—Good, holds firm on tree 8 to 10 days after maturity.

*Aroma*.—Moderate to heavy.

*Amydgalin*.—Undetected.

*Eating quality*.—Good.

*Flavor*.—Good.

*Juice*.—Moderate amount, enhances flavor.

*Brix*.—Average Brix 12.2°, varies slightly with amount of fruit per tree and climatic conditions.

*Color*.—Varies from 2.5Y 8/8 to 2.5Y 8/10 with 5R 4/10 to 7.5R 3/10 bleeding out from the pit cavity.

*Pit cavity*.—Average length 28.3 mm. Average width 26.0 mm. Average depth 9.2 mm. Color varies from 5R 2/4 to 7.5R 3/10.

Skin:

*Thickness*.—Medium.

*Surface*.—Smooth.

*Pubescence*.—Moderate, short in length.

*Tendency to crack*.—None.

*Color*.—Ground color varies from 2.5Y 8/8 to 2.5Y 8/10. Overspread with 7.5R 3/4 to 10R 4/8.

*Tenacity*.—Tenacious to flesh.

*Astringency*.—None.

Stone:

*Type*.—Clingstone.

*Size*.—Large. Average length 27.9 mm. Average width 24.4 mm. Average thickness 17.9 mm.

*Form*.—Ovoid.

*Base*.—Varies from flat to round.

*Apex*.—Rounded.

*Surface*.—Pitted throughout, pits vary from rounded to slightly elongated.

*Sides*.—Unequal, with one side extending further from suture plane.

*Ridges*.—Small ridges extending from base toward apex.

*Tendency to split*.—None.

*Color*.—Varies from 7.5R 2/6 to 10R 2/6 when dry.

Kernel:

*Size*.—Medium. Average length 16.5 mm. Average width 11.6 mm. Average depth 5.9 mm.

*Form*.—Ovoid.

*Viability*.—Viable, complete embryo development.

*Skin color*.—Varies from 2.5Y 8.5/8 to 5Y 8.5/8.

Use: Dessert.

*Market*.—Local and long distance.

Keeping quality: Good, held firm in cold storage at 38° to 42° F. for 3 weeks without internal breakdown of flesh or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

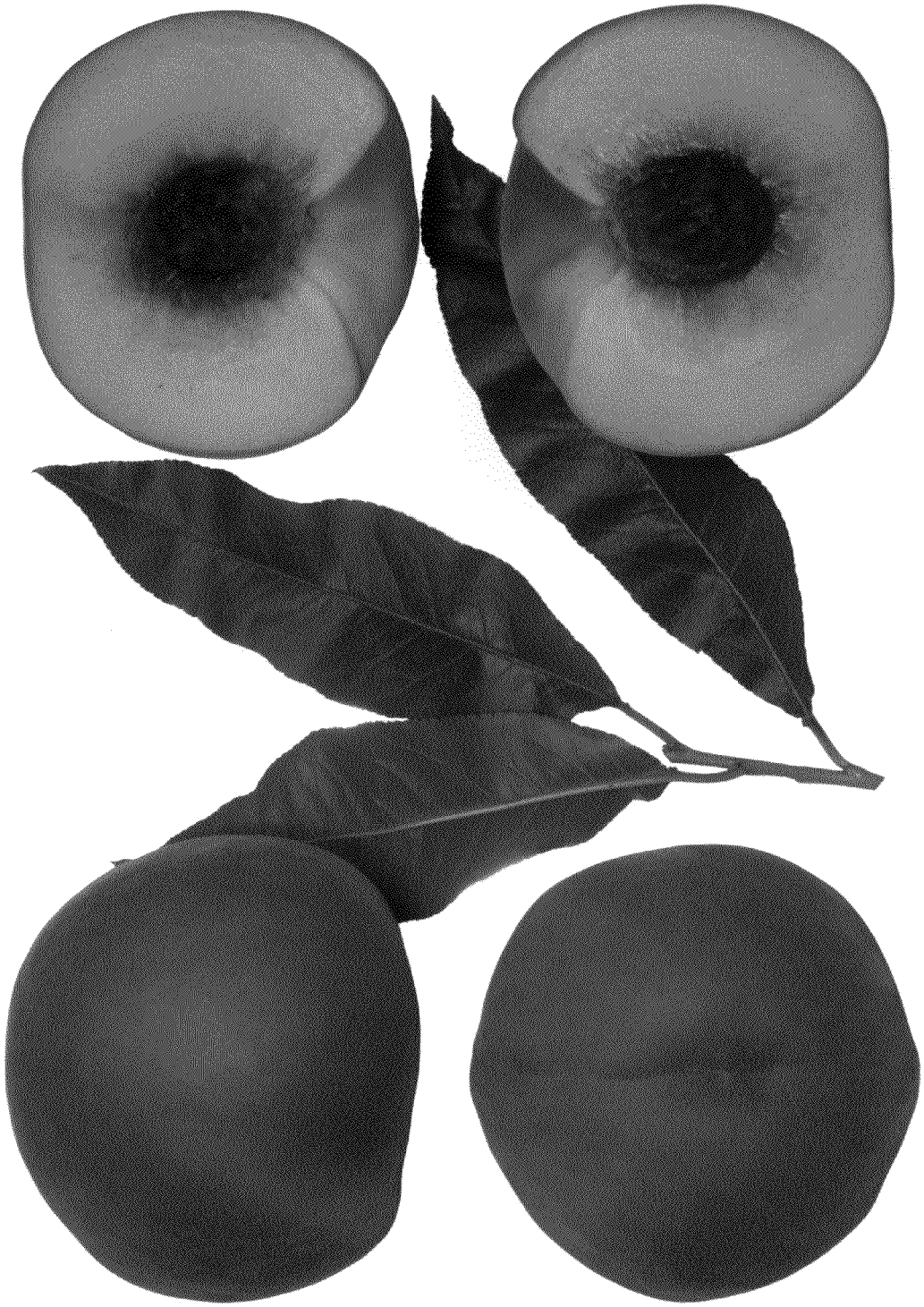

* * * * *